US012797327B2

(12) United States Patent
Lee et al.

(10) Patent No.: US 12,797,327 B2
(45) Date of Patent: Nov. 17, 2026

(54) COMPOSITION FOR IMPROVING SKIN COMPRISING STEAMED CITRUS PEEL EXTRACT AS ACTIVE INGREDIENT

(71) Applicant: LG HOUSEHOLD & HEALTH CARE LTD., Seoul (KR)

(72) Inventors: Gwangjin Lee, Seoul (KR); So Young Lee, Seoul (KR); Mu hyun Jin, Seoul (KR); Yun Hee Chang, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 490 days.

(21) Appl. No.: 18/108,386

(22) Filed: Feb. 10, 2023

(65) Prior Publication Data

US 2023/0255877 A1 Aug. 17, 2023

(30) Foreign Application Priority Data

Feb. 11, 2022 (KR) ........................ 10-2022-0018207
Dec. 9, 2022 (KR) ........................ 10-2022-0171739

(51) Int. Cl.

| | |
|---|---|
| ***A61K 8/9789*** | (2017.01) |
| ***A23L 33/105*** | (2016.01) |
| ***A61K 36/752*** | (2006.01) |
| ***A61P 29/00*** | (2006.01) |
| ***A61Q 19/08*** | (2006.01) |

(52) U.S. Cl.

CPC .......... *A61K 8/9789* (2017.08); *A23L 33/105* (2016.08); *A61K 36/752* (2013.01); *A61P 29/00* (2018.01); *A61Q 19/08* (2013.01); *A61K 2236/17* (2013.01); *A61K 2236/33* (2013.01); *A61K 2800/522* (2013.01); *A61K 2800/805* (2013.01)

(58) Field of Classification Search

CPC ................ A61K 8/9789; A61K 36/752; A61K 2236/17; A61K 2236/33; A61K 2800/522; A61K 2800/805; A61K 8/602; A23L 33/105; A61P 29/00; A61Q 19/08

See application file for complete search history.

(56) References Cited

U.S. PATENT DOCUMENTS

2010/0040696 A1 * 2/2010 Sente ................... A61K 8/9717 424/497

FOREIGN PATENT DOCUMENTS

| | | | | |
|---|---|---|---|---|
| JP | 2021116288 A * | 8/2021 | | |
| KR | 10-2018-0082362 A | 7/2018 | | |
| KR | 10-2021-0048467 A | 5/2021 | | |
| WO | WO-2008034702 A1 * | 3/2008 | ............... | A61K 8/49 |

OTHER PUBLICATIONS

Espacenet Machine Translation of JP-2021116288-A (Aug. 10, 2021) Arifuku, M et al. Accessed May 8, 2025. (Year: 2021).*

B Lapornik et al., "Comparison of extracts prepared from plant by-products using different solvents and extraction time," Journal of Food Engineering 71 (2005) 214-222.*

G. J. Lee et al., "A multi-faceted comparison of phytochemicals in seven citrus peels and improvement of chemical composition and antioxidant activity by steaming," LWT Food Science and Technology 160 (2022) 113297. Available online Mar. 5, 2022.*

C. Dorado et al., "Study of Static Steam Explosion of Citrus sinensis Juice Processing Waste for the Isolation of Sugars, Pectic Hydrocolloids, Flavonoids, and Peel Oil," Food and Bioprocess Technology (2019) 12:1293-1303.*

Bailey et al., "Grapefruit-medication interactions: Forbidden fruit or avoidable consequences?", CMAJ, Nov. 26, 2012, 185: 309-316.

Hung et al., "Chemistry and health effects of furanocoumarins in grapefruit", Journal of Food and Drug Analysis, 2016, 25: 71-83.

Muehldorf et al., "Aromatic-Aromatic Interactions in Molecular Recognition: A Family of Artificial Receptors for Thymine That Shows Both Face-to-Face and Edge-to-Face Orientations", Journal of the American Chemical Society, 1988, 79(24), pp. 6561-6562.

* cited by examiner

*Primary Examiner* — Monica A Shin

(74) *Attorney, Agent, or Firm* — Birch, Stewart, Kolasch & Birch, LLP

(57) ABSTRACT

The present invention relates to cosmetic, food, and quasi-drug compositions having antioxidant, anti-inflammatory, and wrinkle or elasticity improvement effects, comprising citrus peel extracts as an active ingredient, which increase phenolic compounds, increase the generation of flavonoid aglycones, and reduce furanocoumarin, a harmful substance, a method for preparing the same, and citrus peel extracts prepared by the method. The present invention has excellent antioxidant, anti-inflammatory, and wrinkle or elasticity improvement effects, and thus can be used as a cosmetic composition, a food composition, and a quasi-drug composition that are safe for the skin and have excellent skin condition improvement effects.

18 Claims, No Drawings

COMPOSITION FOR IMPROVING SKIN COMPRISING STEAMED CITRUS PEEL EXTRACT AS ACTIVE INGREDIENT

TECHNICAL FIELD

The present invention relates to cosmetic, food, and quasi-drug compositions having antioxidant, anti-inflammatory, and wrinkle or elasticity improvement effects, including citrus peel extracts as an active ingredient, a method for preparing the same, and citrus peel extracts prepared by the method.

BACKGROUND ART

Citrus peel contains many physiologically active substances useful to the human body, such as dietary fiber including pectin, carotenoids, vitamins, and various types of flavonoids (Journal of the American Chemical Society, 79(24), 6561-6562). Various physiological activities of peel-derived flavonoids have been recently reported, and in particular, hesperidin, also referred to as vitamin P, has been reported to be effective in preventing arteriosclerosis and hypertension by protecting capillaries. As such, it has been found that the peel of citrus fruits contains a higher amount of active ingredients with various pharmacological activities than the flesh of citrus fruits, and accordingly, more research is being conducted on the use of peel as food, along with studies on the efficacy of active ingredients derived from the peel of citrus fruits.

Flavonoids are plant-derived polyphenol-based compounds that are mainly present on the surface of fruits and leaves, flowers, etc., and are involved in protecting plants from ultraviolet (UV) rays, plant color, and resistance to diseases and pests. Flavonoids are glycosides and are known to provide stronger physiological effects when converted to non-glycosides (aglycones) through in vivo metabolism. However, acid hydrolysis or fermentation has been reported as a method for converting flavonoid glycosides into non-glycosides in raw materials, but unexpected effects such as the generation of impurities that may occur due to additional mixing of chemicals and microorganisms have yet to be identified in detail. Thus, the method of using flavonoids in cosmetics as a non-glycoside type extract is currently limited.

Furanocoumarins are known to cause phototoxic effects in human skin by plants. This causes skin reactions similar to sunburn (erythema, edema, blisters, etc.) or cell necrosis (J Food Drug Anal, 25: 71-83). Furanocoumarins inhibit the enzymatic activity of the cytochrome P450 family (cytochrome P450 3A4; CYP3A4) present in the liver and small intestine, thereby inactivating drugs activated by CYP3A4, and conversely, drugs that are inactivated by CYP3A4 are activated. As a result, a phenomenon in which the appropriate concentration of the drugs in the blood becomes too low or too high may occur, and the expected drug effect may not appear or serious side effects may occur (CMAJ, 185: 309-316). However, there is no known method for selectively reducing furanocoumarins without a chemically complex process such as purification.

Under these circumstances, the present inventors have developed a method for preparing steamed citrus peel extracts under optimized conditions to improve the composition of citrus peel and promote skin efficacy, and have confirmed that the steamed citrus peel extracts prepared by the method have excellent antioxidant, anti-inflammatory, and wrinkle or elasticity-improvement effects, thereby completing the present invention.

DISCLOSURE

Technical Problem

It is one object of the present invention to provide a cosmetic composition, including a steamed citrus peel extract as an active ingredient.

It is another object of the present invention to provide a food composition, including a steamed citrus peel extract as an active ingredient.

It is still another object of the present invention to provide a quasi-drug composition, including a steamed citrus peel extract as an active ingredient.

It is yet another object of the present invention to provide a method for preparing a citrus peel extract, including: steaming citrus peel; and extracting the steamed citrus peel.

It is even another object of the present invention to provide a citrus peel extract prepared by the method above.

It is further another object of the present invention to provide a cosmetic composition, including the citrus peel extract prepared by the method above as an active ingredient.

Technical Solution

Hereinafter, the present invention will be described in detail. Meanwhile, each description and embodiment disclosed herein can be applied to other descriptions and embodiments with respect to common features. That is, all combinations of various elements disclosed herein fall within the scope of the present invention. Further, the scope of the present invention is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present invention.

One aspect to achieve the objects above, the present invention provides a cosmetic composition, including a steamed citrus peel extract as an active ingredient.

As used herein, the term "citrus" is a generic name over the three genera of *Citrus, Fortunella*, and *Poncirus* of the citrus family. The citrus refers to fruits and immature fruits thereof included in the citrus family such as satsuma mandarin, kumquat, trifoliate orange, citron, pomelo mandarin, tangerine, sweetie, citron, citrus sudachi, cheonhyehyang, calamansi, pomelo, hanrabong, orange, bitter orange, lemon, grapefruit, lime, yuzu, etc., and is not particularly limited as long as the citrus belongs to the citrus plant. Specifically, in the present invention, the citrus may be satsuma mandarin, yuzu, orange, bitter orange, grapefruit, lemon, or lime, but is not limited thereto.

As used herein, the "peel" refers to the skin covering the outer side of the pulp, and is divided into an exocarp, a mesocarp, and an endocarp in the botanical meaning. Flavonoids present in citrus are classified into six groups, i.e., flavones, flavanones, flavonols, isoflavones, anthocyanidins, flavanols, etc. depending on the molecular structure, and flavanones are especially abundant in the skin and seeds rather than in the flesh. In the present invention, the citrus peel may refer to the exocarp and the mesocarp among the exocarp, mesocarp, and endocarp, but is not limited thereto.

The citrus peel may contain various compounds, such as narirutin, naringin, and hesperidin as flavonoid glycones, naringenin and hesperetin as flavonoid aglycones, and bergapten and bergamottin as furanocoumarin, etc.

As used herein, the term "flavonoid" is a yellow pigment widely distributed in food, and is a plant-derived polyphenolic compound. Flavonoids are present in a relatively small amount in animals and are abundant in leaves, flowers, roots, fruits, and stems of plants, and are mainly used in health supplement, medicinal drug, and cosmetic industries because they play a role in antioxidant, anti-inflammatory, anti-mutagenic, anticancer, and function control of major enzymes.

As used herein, the term "glycone" is a generic term for molecules in which sugar molecules are linked to other functional groups through glycosidic bonds, and are mainly found in plants. Many glycones are known to be active when sugar molecules are hydrolyzed by hydrolysis. Glycones are broken down into sugar moieties, and non-sugar moieties referred to as aglycones or genin by the action of acids, alkali, or suitable hydrolases.

The flavonoid glycones may include, for example, narirutin, naringin, hesperidin, didymin, limocitrin, eriocitrin, neoeriocitrin, neohesperidin, poncirin, and neoponcirin, etc., without limitation, and the flavonoid glycones of the citrus may typically include narirutin, naringin, or hesperidin, but are not limited thereto.

The "narirutin" is known to have effects of increasing activity in the body, anticancer activity, and improving alcoholic liver disease, and the "naringin" has an anticancer activity and a blood fat lowering effect. The "hesperidin" is known to act as a defense mechanism for plants and soothes stressed skin cells.

As used herein, the term "aglycone" refers to a non-carbohydrate (non-sugar component) in a glycoside molecule, and it is known that glycones provide stronger physiological efficacy when converted to aglycone.

The flavonoid aglycones may include, for example, naringenin, hesperetin, eriodictyol, isosakuranetin, etc. without limitation, and the flavonoid aglycones of citrus may typically include naringenin or hesperetin, but are not limited thereto.

The "naringenin" is known to have antibacterial, and anticancer activities, and narirutin or naringin is converted to low-molecular naringenin by the action of acids, alkali, or suitable hydrolytic enzymes. The "hesperetin" is abundant in citrus fruits and has a muscle regenerative effect, and hesperidin (hesperetin-based glycosides) is converted to low-molecular hesperetin by the action of acids, alkali, or suitable hydrolytic enzymes.

The present invention is characterized in that the content of flavonoid aglycones contained in the steamed citrus peel extract can be increased by converting flavonoid glycones into aglycones through the steaming process.

In the present invention, the steaming may be performed at 103° C. to 150° C., specifically at 105° C. to 130° C., more specifically at 120° C., for 1 hour to 15 hours or 1 hour to 12 hours, specifically 2 hours to 8 hours, and more specifically 4 to 8 hours, but is not limited thereto.

As used herein, the term "furanocoumarin" is a secondary metabolite produced in plants and is a generic term for coumarin compounds to which a furan ring is bonded. It is known that many types of furanocoumarins are phototoxic and can cause phytophotodermatitis in human skin and cause drug-related side effects.

The furanocoumarin may include, for example, bergaptol, bergapten, bergamottin, epoxybergamotin, etc. without limitation, and the furanocoumarin of the citrus may typically include bergapten or bergamottin, but is not limited thereto.

The "bergapten" is a non-volatile phototoxic (sensory) component, which may cause dermatitis, and may promote erythema by increasing UV sensitivity of the skin, or increase melanin pigment (pigmentation). The "bergamottin" inhibits cytochrome P450, which is essential for the normal metabolism of drugs in the body, thereby preventing oxidative metabolism of a specific drug by enzymes and increasing the concentration of the drug in the bloodstream.

The present invention is characterized in that the content of furanocoumarin, which is a harmful substance, can be lowered through the steaming process.

In a specific embodiment of the present invention, in the case of citrus species that were not steamed, flavonoid glycones were detected, whereas flavonoid aglycones were not detected, and furanocoumarin was detected only in some of the peels (Table 1).

As used herein, the term "steaming" means steaming by applying temperature and steam. The device used for steaming is not limited as long as the steaming can be performed at a constant temperature and pressure.

Specifically, steaming may be performed in an airtight container, and more specifically, may be performed in a thick airtight stainless steel container, but is not limited thereto. Since the steaming process is performed in a completely airtight container, the reaction may occur in a state in which a high pressure is maintained, but is not limited thereto.

In a specific embodiment of the present invention, when roasting was performed at 120° C. for 8 hours, instead of steaming, there was no significant change in the content of flavonoid glycones and aglycones, and when roasting was performed at a higher temperature of 200° C. for 5 minutes, the outer surface of the raw material was easily burned without a significant change in components, confirming that hesperidin could not be converted to hesperetin. In addition, when steaming was performed at a low temperature of 100° C. or less, an excess amount of steam was not generated and thus the pressure was low. Even when heat treatment was prolonged by increasing the steaming treatment time (low pressure, low temperature), the flavonoid glycones were not converted to aglycones, thereby confirming that aglycones were significantly generated only when steamed at a high temperature of 105° C. to 130° C. in an airtight container (Table 9).

Specifically, flavonoid glycones were reduced by decomposition by heat at the beginning (30 minutes of steaming, 2 hours or 4 hours of steaming), and after some recovery due to the increase in extraction efficiency, it tended to decrease again (after 4 or 8 hours of steaming).

The increase in extraction efficiency is due to a physicochemical change, and specifically, the physicochemical change means an increase in the surface area of the particles, which is confirmed by a decrease in volume per unit weight when the peel is steamed and then powdered.

The flavonoid aglycones started to appear from 2 hours of steaming, and at 8 hours of steaming, the flavonoid aglycones were increased by more than 6.5 times at maximum compared to the initial stage, thereby confirming that the flavonoid aglycones were converted into low-molecular aglycones, which are effective forms of absorption in the body. In the case of furanocoumarin, it decreased during steaming, and although some amount was recovered at 8 hours of steaming, it tended to decrease again after 8 hours of steaming, confirming that the amount of harmful substances decreased (Tables 2 to 8).

As used herein, the term "phenolic compounds" are substances widely distributed in the plant kingdom and have various structures and molecular weights, and it is known that the phenolic hydroxyl group of phenolic compounds has physiological functions such as antioxidant, anticancer, and antibacterial properties through binding to macromolecules such as proteins. Additionally, the DPPH radical scavenging activity is believed to be highly correlated with the total phenolic content.

In a specific embodiment of the present invention, the total content of phenolic compounds tended to decrease at the beginning of steaming, similar to flavonoid glycones, and thereafter, the reduced amount was partially recovered, and at 8 hours of steaming, the total content of phenolic compounds significantly increased compared to the initial stage, indicating that the antioxidant activity was increased (Table 10).

As used herein, the term "extract" refers to a resulting product, such as a liquid component which is obtained by immersing a desired material in various solvents followed by extracting for a predetermined period of time at room temperature, at low temperature, or in a heated state; a solid component which is obtained by removing the solvent from the liquid component; etc. Moreover, the extract may be comprehensively interpreted to include all of a diluted solution of the resulting products, a concentrated solution thereof, a crude product thereof, a purified product thereof, etc., in addition to the above resulting products. Accordingly, the citrus peel extract provided in the present invention may be interpreted to include the extract itself and extracts of all formulations that can be formed using the extract solution, such as an extract obtained by extracting the citrus peel extract, a diluted or concentrated solution of the extract, a dried product obtained by drying the extract, a crude or purified product of the extract, or a mixture thereof.

The method for extracting the citrus peel of the present invention is not particularly limited, and the citrus peel may be extracted according to a method commonly used in the art. Non-limiting examples of the extraction method include a cold extraction method, a hot water extraction method, an ultrasonic extraction method, a filtration method, a reflux extraction method, a $CO_2$ extraction method, etc., which may be performed alone or in combination of two or more methods.

The kind of solvents used for extraction is not particularly limited, and any solvent known in the art may be used. Non-limiting examples of the extraction solvent may include water, alcohol, or a mixed solvent thereof, and these solvents may be used alone or in a combination of two or more kinds, and specifically, water may be used. When alcohol is used as a solvent, a $C_{1-4}$ alcohol may specifically be used.

Additionally, the extract may be prepared in a dry powder form after extraction to be used, but is not limited thereto.

In the present invention, the "steamed citrus peel extract" may be obtained by steaming dried citrus, followed by drying, and then extracting with methanol or ethanol, but is not limited thereto.

In a specific embodiment of the present invention, the methanol extract was used for the evaluation of components, and the components of the methanol and ethanol extracts were almost similar, but the ethanol extract was used for efficacy evaluation in consideration of safety in actual industrial application.

The cosmetic composition including the steamed citrus peel extract of the present invention may be used for skin improvement.

As used herein, the "skin improvement" may be any one or more selected from the group consisting of antioxidant, anti-inflammatory, and wrinkle or elasticity improvement, but is not limited thereto.

As used herein, the term "improvement" refers to all activities that at least reduce the parameters associated with alleviation or treatment of conditions; e.g., the degree of symptoms, and may include any one or more selected from antioxidant, anti-inflammatory, and wrinkle or elasticity improvement.

The skin improvement may be achieved through scavenging free radicals, inhibiting NO production, and promoting collagen synthesis, but is not limited thereto.

Specifically, the present inventors confirmed that the skin improvement effect of the steamed citrus peel extracts was superior compared to that of non-steamed extracts. More specifically, the steamed citrus peel extracts showed an increased phenolic compound content, and the activities of free radical scavenging, NO production inhibition, and collagen synthesis promotion were markedly increased. Therefore, it was confirmed in the present invention that the steamed citrus peel extracts have excellent skin improvement effects such as antioxidation, anti-inflammation, and wrinkle or elasticity improvement, compared to the case without steaming treatment.

As used herein, the term "anti-oxidative" means to include all actions of inhibiting oxidation, and may specifically means an action of removing free radicals such as reactive oxygen species, etc., but is not limited thereto. The human body maintains a balance between pro-oxidants and anti-oxidants. However, when this balance is disrupted by various factors, the body is inclined toward a direction of promoting oxidation, resulting in induction of oxidative stress. This oxidative stress has the potential to cause cellular damage and lead to pathological disease. Reactive oxygen species (ROS), which are a direct cause of such oxidative stress, are unstable and highly reactive, and thus, they can easily react with various biomaterials and attack the polymers in the body, causing irreversible damage or mutations, cytotoxicity, carcinogenesis, etc. to cells and tissues. The reactive nitrogen species (RNS), such as NO, $HNO_2$, and $ONOO^-$, are produced in large amounts due to the immune response of macrophage neutrophils and other immune cells during an inflammatory response, and at this time, ROS are also produced as well. Such ROS can oxidize and destroy cells in the body, thereby exposing them to various diseases. Therefore, the composition including the steamed citrus peel extract of the present invention can contribute to promoting health by antioxidant activity through free radical scavenging and NO production inhibition.

As used herein, the term "free radical" refers to an atom or molecule having one unpaired electron. A hydrogen atom, a chlorine atom, etc. are monoatomic radicals, and in general, a radical refers to a molecule which releases a proton from an inorganic or organic compound molecule and thus has an unpaired electron in the residue. Active oxygen species have excellent chemical reactivity, and radicals induced thereby affect various reactions in the body and cause aging, etc. Organisms are always exposed to free radicals causing harmfulness, and as cells age, harmfulness gradually accumulates, thereby causing various diseases. Thus, free radical scavenging plays an important role against the effects of oxidation.

In a specific embodiment of the present invention, as a result of treatment with the citrus extract steamed at 120° C.

for 8 hours, free radicals were scavenged, and the level thereof was higher than that of the untreated case (Table 11).

The steamed citrus extract not only had increased flavonoid contents and total phenolic contents, but also showed increased free radical scavenging ability, thus confirming the effect of enhancing antioxidant activity. The citrus extract whose antioxidant activity was enhanced by the steaming treatment can be effectively used in cosmetic compositions.

As used herein, the term "anti-inflammatory" means to include all actions of inhibiting inflammation, and in general, refers to the prevention, treatment, or improvement of inflammation. Inflammation reactions are induced to enhance the in vivo restoration systems and reduce the damage thereof, and if the inflammation is severe or lasts for a long time, cells are damaged, leading to various inflammatory diseases. Specifically, it may inhibit the production of inflammation-related mediators or reactive oxygen species (ROS), and the inflammation-related mediator may be nitric oxide (NO), but is not limited thereto.

As used herein, the term "NO (nitric oxide)" plays various roles such as removing bacteria and tumors, regulating blood pressure, or mediating nerve transmission. However, in the presence of an inflammatory reaction, the expression of iNOS (inducible nitric oxide synthase) increases in related cells, leading to an excess production of NO. Further, the excess production of NO causes tissue damage, genetic mutation, nerve damage, etc., and increases vascular permeability, thereby promoting inflammatory responses such as edema. While the production of NO is increased in inflamed cells, the production of NO is suppressed when the skin is soothed, and there exists an essential correlation therebetween.

In a specific embodiment of the present invention, as a result of treatment with the citrus extract steamed at 120° C. for 8 hours, the production of NO was inhibited, and the inhibition level was superior to that of untreated cases (Table 12).

As used herein, the term "wrinkles" can be largely divided into facial wrinkles caused by facial expression muscles used to make facial expressions and fine wrinkles caused by overall or localized skin weakness. Specifically, wrinkles may be caused by genes, a decrease in collagen and elastic fibers present in the skin dermis, an external environment, etc. For the purpose of the present invention, wrinkles may be used in the sense of including all facial wrinkles or fine wrinkles, but is not limited thereto.

As used herein, the term "elasticity" is the force that tightly holds the skin when it is pressed with a finger. The term "elasticity improvement" or "elasticity enhancement" refers to increasing the elasticity of the skin by strengthening the structure of the subcutaneous fat layer of an individual, and may refer to increasing skin elasticity by the composition of the present invention.

As used herein, the term "aging" refers to a natural phenomenon in which biological structures and functions deteriorate over time, and the anti-aging of the present invention is not limited to an extent as long as aging is improved, such as preventing, suppressing, or delaying aging. The wrinkle improvement and anti-aging in the present invention may be caused by promoting collagen synthesis, but is not limited thereto.

As used herein, the term "collagen" refers to a fibrous protein largely found in most animals, particularly mammals, covering almost all connective tissues in the body, such as skin and cartilage, and fibroblasts, the most common cells in the body, produce and secrete collagen. Gelatin, which is widely used in cooking or in the food and pharmaceutical industries, is the product obtained by irreversible hydrolysis of collagen. Since the decrease in collagen causes wrinkles and is the main cause of reducing skin elasticity, synthesis of collagen is essential for improving wrinkles and enhancing elasticity.

In a specific embodiment of the present invention, as a result of treatment with the citrus extract steamed at 120° C. for 8 hours, the amount of additional collagen production increased, and the increase level was superior to that of untreated cases (Table 14).

Since the "cosmetic composition of the present invention" is designed to be applied to the skin, it can be prepared into any formulation conventionally prepared by referring to the cosmetic compositions of the related art. For example, it may be prepared in the form selected from the group consisting of solution, ointment for external use, cream, foam, nutritive cosmetic water, softening cosmetic water, facial mask, softening water, makeup base, foundation, essence, soap, liquid washing agent, bath foam, sunscreen cream, sun oil, suspension, gel, lotion, powder, surfactant-containing cleanser, patch and spray, but is not limited thereto.

The cosmetic composition may further include conventional auxiliary agents and carriers such as antioxidants, stabilizers, solubilizers, vitamins, pigments, fragrances, etc., which are conventionally used in cosmetic compositions, in addition to the steamed citrus peel extract of the present invention. For example, the cosmetic composition may further include an auxiliary component such as glycerin, butylene glycol, polyoxyethylene hardened castor oil, tocopheryl acetate, citric acid, panthenol, squalane, sodium citrate, allantoin, etc.

The cosmetic composition may be formulated in various forms, including softening cosmetic water, astringent cosmetic water, nutritive cosmetic water, nutritive cream, massage cream, essence, facial mask, skin adhesive patch, skin adhesive gel, powder, ointment, paste, gel, suspension, emulsion, spray, cosmetic liquid, or capsule, but is not particularly limited thereto.

Additionally, the cosmetic composition of the present invention may further include one or more cosmetically acceptable carriers mixed to a general skin cosmetic composition. As common ingredients, for example, oil, water, surfactants, moisturizers, lower alcohols, thickening agents, chelating agents, colorings, preservatives, fragrances, etc. may be appropriately mixed, but are not limited thereto. The cosmetically acceptable carrier included in the cosmetic composition of the present invention may vary depending on the formulations.

When the formulation of the present invention is an ointment, paste, cream or gel, animal oil, vegetable oil, wax, paraffin, starch, tragacanth, cellulose derivatives, polyethylene glycol, silicone, bentonite, silica, talc, zinc oxide, or a mixture thereof may be used as a carrier ingredient.

When the formulation of the present invention is a powder or spray, lactose, talc, silica, aluminum hydroxide, calcium silicate, polyamide powder, or a mixture thereof may be used as a carrier ingredient, and in particular, when it is a spray, a propellant such as chlorofluorohydrocarbon, propane/butane or dimethyl ether may be additionally included.

When the formulation of the present invention is a solution or emulsion, solvents, solubilizing agents or emulsifying agents may be used as a carrier ingredient, and for example, water, ethanol, isopropanol, ethyl carbonate, ethyl acetate, benzyl alcohol, benzyl benzoate, propylene glycol, 1,3-butyl glycol oil, may be used. In particular, cottonseed oil, peanut oil, maize germ oil, olive oil, castor oil and sesame seed oil, glycerol aliphatic ester, polyethylene glycol or aliphatic ester of sorbitan may be used.

When the formulation of the present invention is a suspension, liquid diluents such as water, ethanol or propylene glycol, suspending agent, such as ethoxylated isostearyl alcohol, polyoxyethylene sorbitol ester and polyoxyethylene sorbitan ester, microcrystalline cellulose, aluminum metahydroxide, bentonite, agar, or tragacanth may be used as a carrier ingredient.

Meanwhile, when the formulation of the present invention is a capsule, it may be formulated in the form of an alginate capsule, an agar capsule, a gelatin capsule, a wax capsule, or a double capsule, but is not particularly limited thereto.

Another aspect of the present invention provides a food composition including a steamed citrus peel extract as an active ingredient.

As used herein, the term "food" may include all foods in a conventional sense, such as meats, sausages, breads, chocolates, candies, snacks, cookies, pizzas, ramens, other noodles, gums, dairy products including ice cream, various kinds of soups, beverages, teas, drinks, alcoholic beverages, vitamin complexes, health functional foods, etc., and is not limited as long as it can include the steamed citrus peel extract of the present invention. Additionally, the food composition may be added to extracted juice, teas, jellies, juices, etc. which were prepared by adding the steamed citrus peel extract according to the present invention as the main ingredient, and may be prepared in the form of pills, powders, granules, tablets, capsules, or liquids.

When preparing the food composition, it may be prepared by adding raw materials and ingredients commonly added in the art, and the type thereof is not particularly limited. For example, it may include several herbal extracts, sitologically acceptable food additives, or natural carbohydrates as additional ingredients, as in the case of the conventional foods, but is not limited thereto. The mixing amount of the active ingredient may be appropriately determined depending on the purpose of use, and since the composition of the present invention uses an extract derived from a natural product as an active ingredient, the mixing amount is not particularly limited.

The "steaming", "citrus", "peel" and "extract" are as described above.

The food composition may have antioxidant, anti-inflammatory, and wrinkle or elasticity improvement uses, but is not limited thereto.

Still another aspect of the present invention provides a quasi-drug composition including a steamed citrus peel extract as an active ingredient.

As used herein, the term "quasi-drug" refers to articles that are less effective than drugs among those used for the purpose of diagnosing, treating, ameliorating, alleviating, treating or preventing diseases of humans or animals. For instance, according to the Pharmaceutical Affairs Law, quasi-drugs exclude articles for use as drugs and encompass products that are used for treating or preventing diseases of humans and animals, and products which minimally act on the human body or do not act directly on the human body.

Specifically, the quasi-drug may include external skin preparations and personal hygiene products.

More specifically, the quasi-drug may be in the form of a disinfectant, shower foam, a mouth wash, a wet tissue, a detergent soap, a hand wash, or an ointment, but is not limited thereto.

When the composition of the present invention is used as a quasi-drug additive, the composition may be added as-is or used together with other quasi-drugs or quasi-drug components, and may be appropriately used according to a conventional method. The mixing amount of the active ingredient may be appropriately determined depending on the purpose of use.

The "steaming", "citrus", "peel" and "extract" are as described above.

The quasi-drug composition may have antioxidant, anti-inflammatory, and wrinkle or elasticity improvement uses, but is not limited thereto.

Yet another aspect of the present invention provides a method for preparing a citrus peel extract, including: steaming citrus peel; and extracting the steamed citrus peel.

In the present invention, the steaming may be performed at 103° C. to 150° C., specifically at 105° C. to 130° C., more specifically at 120° C., for 1 hour to 15 hours or 1 hour to 12 hours, specifically 2 hours to 8 hours, and more specifically 4 to 8 hours, but is not limited thereto The citrus of the present invention is not particularly limited as long as it belongs to the citrus plant, and specifically, in the present invention, the citrus may be satsuma mandarin, yuzu, orange, bitter orange, grapefruit, lemon, or lime, but is not limited thereto.

In the present invention, the citrus extract may convert flavonoid glycones to low-molecular flavonoid aglycones or reduce the generation of furanocoumarin upon steaming treatment as compared to untreated cases, but is not limited thereto.

The present invention may further include drying after steaming, but is not limited thereto.

In the present invention, the steamed citrus peel extract may have an antioxidant use, but is not limited thereto.

In the present invention, the steamed citrus peel extract may have an anti-inflammatory use, but is not limited thereto.

In the present invention, the steamed citrus peel extract may be used for improving elasticity or wrinkles, but is not limited thereto.

The "steaming", "citrus", "peel", "extract", "antioxidant", "anti-inflammation", and "wrinkle and elasticity improvement" are as described above.

Even another aspect of the present invention provides a citrus peel extract prepared by the method above.

The "steaming", "citrus", "peel" and "extract" are as described above.

The steamed citrus peel extract according to the present invention may have effects of scavenging free radicals, inhibiting NO production, and promoting collagen synthesis, thereby exhibiting antioxidant, anti-inflammatory, and wrinkle or elasticity improvement effects, but is not limited thereto.

Further another aspect of the present invention provides a composition including a citrus peel extract prepared by the method above as an active ingredient.

The composition may be a cosmetic, food, or quasi-drug composition.

The "steaming", "citrus", "peel", "extract", "cosmetic composition", "food", and "quasi-drug" are as described above.

Still further another aspect of the present invention provides an antioxidant method, including applying the steamed citrus peel extract or the composition to a subject.

The "steaming", "citrus", "peel", "extract" and "composition" are as described above.

As used herein, the term "subject" may refer to all animals including humans who have hair loss or likely to have hair loss. The animal may include humans as well as mammals such as cows, horses, sheep, pigs, goats, camels, antelopes, dogs, cats, etc., in need of treating similar symptoms, but is not limited thereto.

In the present invention, the "applying step" refers to the process of applying to the skin. Specifically, as used herein, the term "applying" refers to all methods of contacting the composition of the present invention with the skin of a subject by any suitable method in order for the composition to be absorbed into the skin.

When the composition of the present invention is applied to the skin of a subject, it may have antioxidant, whitening, anti-inflammatory or skin regeneration effects, and may include applying the composition to the subject in an amount effective to exhibit the effects above.

Still further another aspect of the present invention provides a method for preventing or improving inflammation, including applying the steamed citrus peel extract or the composition to a subject.

The "steaming", "citrus", "peel", "extract", "composition", "inflammation prevention" and "improvement" are as described above.

In the present invention, the inflammation prevention or improvement may be used interchangeably with antioxidant.

Still further another aspect of the present invention provides a method for improving elasticity or wrinkles, including applying the steamed citrus peel extract or the composition to a subject.

The "steaming", "citrus", "peel", "extract", "composition", "elasticity" and "wrinkle improvement" are as described above.

Advantageous Effects

The present invention relates to a steamed citrus extract which increases phenolic compounds and the generation of flavonoid aglycones, and reduces furanocoumarin, a harmful substance, and has excellent antioxidant, anti-inflammatory, and wrinkle or elasticity improvement effects, and thus can be used as a cosmetic composition, a food composition, and a quasi-drug composition that are safe for the skin and have excellent skin condition improvement effects.

DETAILED DESCRIPTION OF EMBODIMENTS

Hereinafter, the present invention will be described in more detail by way of Examples. However, these Examples are given for illustrative purposes only, and the scope of the invention is not intended to be limited by these Examples.

Example 1. Preparation of Steamed Citrus Peel Extracts

Example 1-1. Preparation of Citrus Peels and Steaming Thereof

The contaminants on the surface of satsuma mandarin (*Citrus unshiu*), yuzu (*Citrus junos*), orange (*Citrus sinensis*), bitter orange (*Citrus aurantium*), grapefruit (*Citrus paradisi*), lemon (*Citrus limonum*) and lime (*Citrus aurantifolia*) distributed in Korea were carefully washed, and the peels were separated from the inner pulp. After completely drying the separated peels at 40° C., they were cut into a uniform size of about 0.5 cm.

In addition, the cut citrus peels were placed in a thick airtight stainless-steel container under the condition where they could be moistened with a small amount of purified water, and the container was sealed so that outside air could not pass through. Thereafter, steaming was carried out at 120° C. under various steaming time conditions (untreated, 30 minutes, 2 hours, 4 hours, 8 hours and 12 hours). Then, the peels were sufficiently dried at 40° C. until completely dried.

Example 1-2. Preparation of Steamed Citrus Peel Extracts for Evaluation of Components 10 g of the steamed citrus peels were powdered, mixed with 100 mL of high-performance liquid chromatography (HPLC) grade methanol, and sonicated for 1 hour. The extraction process was repeated three times to obtain a total of 300 mL of extraction solvent. 300 mL of the thus-obtained extraction solvent was concentrated and re-adjusted to 100 mL, and filtered through a PTFE filter (0.45 μm) to prepare citrus peel extracts.

In the case of evaluating the flavonoid content or furanocoumarin content described below, the steamed citrus peel extract solution, which was concentrated by the method above, was used, and in the case of evaluating the total content of phenolic compounds, the concentration of the concentrated steamed citrus peel extract solution was diluted by half with methanol and used.

Example 1-3. Preparation of Steamed Citrus Peel Extracts for Efficacy Evaluation 10 g of the steamed citrus peels were powdered, mixed with 100 mL of ethanol, and sonicated for 1 hour. The extraction process was repeated three times to obtain a total of 300 mL of extraction solvent. 300 mL of the thus-obtained extraction solvent was concentrated and re-adjusted to 100 mL, and filtered through a PTFE filter (0.45 μm) to prepare citrus peel extracts.

In the case of confirming the antioxidant effect described below, the concentration of the concentrated steamed citrus peel extract solution was diluted by half with ethanol and used.

In the case of confirming anti-inflammatory effect and collagen synthesis-promoting effect, ethanol was completely removed from the steamed citrus peel extract solution using a rotary evaporator, and the residue was redissolved in DMSO so that the extract solution had a final concentration of 50,000 ppm and used.

Example 2. Change in Components According to Steaming Treatment Time and Heat Treatment Conditions and Comparison of Contents

Example 2-1. Analysis of Peel Components According to Citrus Species

In order to analyze the peel components according to the citrus species, the contents of flavonoid glycones, flavonoid aglycones, and furanocoumarins of non-steamed satsuma mandarin, yuzu, orange, bitter orange, grapefruit, lemon or lime were compared (Table 1).

The content (mg) of narirutin, naringin and hesperidin, which are three flavonoid glycones; naringenin and hesperetin, which are two flavonoid aglycones; and bergapten and bergamottin, which are two furanocoumarins, contained in 100 g of dried citrus peels was evaluated using high-performance liquid chromatography (HPLC) and diode array detector (DAD) manufactured by Shimadzu.

Specifically, the components in the extracts were analyzed by a gradient elution method using ZORBAX Eclipse Plus reversed-phase column (4.6×150 mm, 3.5 μm particle size) manufactured by Agilent as the stationary phase, and a combination of water added with a small amount of formic acid and acetonitrile as the mobile phase. The sample input amount was 10 μL, the flow rate was 1 mL/min, and the detection wavelengths were 283 and 310 nm. Standards for qualitative and quantitative analyses were purchased from Sigma-Aldrich, and a calibration curve was prepared using absorbance values according to five or more concentrations to calculate the content in the extract (average value, n=3).

TABLE 1

| Contents (mg/100 g) | Satsuma mandarin | Yuzu | Orange | Bitter orange | Grapefruit | Lemon | Lime |
|---|---|---|---|---|---|---|---|
| Narirutin | 1064.2 | 473.4 | 134.2 | 6.4 | 282.7 | 18.5 | 55.9 |
| Naringin | 14.6 | 525.5 | N.D. | 1975.0 | 3131.4 | 13.4 | 3.6 |
| Hesperidin | 2149.6 | 536.7 | 1629.9 | N.D. | N.D. | 640.0 | 486.2 |
| Total | 3228.4 | 1535.6 | 1764.1 | 1981.4 | 3414.1 | 671.9 | 545.7 |
| Naringenin | N.D. | N.D. | N.D. | N.D. | N.D. | N.D. | N.D. |
| Hesperetin | N.D. | N.D. | N.D. | N.D. | N.D. | N.D. | N.D. |
| Total | N.D. | N.D. | N.D. | N.D. | N.D. | N.D. | N.D. |
| Bergapten | N.D. | N.D. | N.D. | 6.4 | N.D. | 0.3 | 19.6 |
| Bergamottin | N.D. | N.D. | N.D. | N.D. | 2.5 | 1.6 | 8.1 |
| Total | N.D. | N.D. | N.D. | 6.4 | 2.5 | 1.9 | 27.7 |

As shown in Table 1, there were differences in the content or composition of flavonoid glycones for each citrus species, and flavonoid aglycones were not detected in the peels that were not steamed (Not Detected, N.D.). Additionally, bergapten or bergamottin, a furanocoumarin, was detected in 4 of the 7 types of peels (bitter orange, grapefruit, lemon, lime).

In Examples 2-2 to 2-8 below, changes in the components of flavonoid glycones, flavonoid aglycones, and furanocoumarins (mg contained in 100 g of citrus) according to the steaming treatment time conditions for each citrus species were confirmed.

Example 2-2. Change in Components According to Steaming Treatment Time of Satsuma Mandarin Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of satsuma mandarin, a citrus species (Table 2).

As a result, in the case of flavonoid glycones (narirutin, hesperidin), they were decomposed and reduced by heat in the initial stage with increasing steaming time (untreated, steamed for 30 minutes, steamed for 2 hours, steamed for 4 hours). However, after that (steamed for more than 4 hours, steamed for 8 hours), it was confirmed that the content of flavonoid glycones, which had been reduced, was increased and partially recovered as the extraction efficiency was increased due to the physicochemical change of the peels by the steaming treatment. After 8 hours of steaming, it showed a tendency to decrease again. However, naringin tended to increase because the increase in the extraction efficiency was superior due to the physicochemical changes than the decomposition by heat.

In the case of flavonoid aglycones, they started to appear from 2 hours of steaming, and at 8 hours of steaming, the content thereof was increased by about 1.6 to 2 times or more compared to the initial stage, confirming that the flavonoid glycones were converted to low-molecular aglycones. After 8 hours of steaming, it showed a tendency to decrease again.

The components of furanocoumarins were not detected under untreated and steam-treated conditions.

TABLE 2

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 1064.2 | 998.3 | 669.2 | 622.7 | 655.9 | 415.1 |
| Naringin | 14.6 | 17.1 | 43.2 | 55.5 | 98.3 | 70.8 |
| Hesperidin | 2149.6 | 1893.4 | 879.4 | 700.5 | 1092.2 | 693.1 |
| Total | 3228.4 | 2908.8 | 1591.8 | 1378.7 | 1846.4 | 1179.0 |
| Naringenin | N.D. | N.D. | 10.1 | 15.0 | 22.9 | 13.1 |
| Hesperetin | N.D. | N.D. | 8.5 | 16.4 | 28.5 | 13.8 |
| Total | N.D. | N.D. | 18.6 | 31.4 | 51.4 | 26.9 |
| Bergapten | N.D. | N.D. | N.D. | N.D. | N.D. | N.D. |
| Bergamottin | N.D. | N.D. | N.D. | N.D. | N.D. | N.D. |
| Total | N.D. | N.D. | N.D. | N.D. | N.D. | N.D. |

Example 2-3. Change in Components According to Steaming Treatment Time of Yuzu Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of yuzu, a citrus species (Table 3).

As a result, in the case of flavonoid glycones, it was confirmed that the content of flavonoid glycones decreased due to decomposition by heat as the steaming time increased.

In the case of flavonoid aglycones, they started to appear from 2 hours of steaming, and at 8 hours of steaming, the content thereof was increased by about 1.6 to 2 times or more compared to the initial stage, confirming that the flavonoid glycones were converted to low-molecular aglycones. After 8 hours of steaming, it showed a tendency to decrease again.

The components of furanocoumarins were not detected under untreated and steam-treated conditions.

TABLE 3

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 473.4 | 451.9 | 397.6 | 363.8 | 247.3 | 249.5 |
| Naringin | 525.5 | 518.7 | 478.9 | 490.2 | 410.8 | 404.8 |
| Hesperidin | 536.7 | 511.0 | 453.6 | 398.0 | 282.4 | 283.5 |
| Total | 1535.6 | 1481.6 | 1330.1 | 1252.0 | 940.5 | 937.8 |
| Naringenin | N.D. | N.D. | 15.9 | 25.6 | 26.5 | 21.9 |
| Hesperetin | N.D. | N.D. | 14.0 | 23.6 | 30.1 | 25.4 |
| Total | N.D. | N.D. | 29.9 | 49.2 | 56.6 | 47.3 |
| Bergapten | N.D. | N.D. | N.D. | N.D. | N.D. | N.D. |
| Bergamottin | N.D. | N.D. | N.D. | N.D. | N.D. | N.D. |
| Total | N.D. | N.D. | N.D. | N.D. | N.D. | N.D. |

Example 2-4. Change in Components According to Steaming Treatment Time of Orange Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of orange, a citrus species (Table 4).

As a result, in the case of flavonoid glycones (narirutin, hesperidin), it was confirmed that the content of hesperidin was more than 12 times higher compared to that of narirutin. Additionally, the two substances were decomposed and reduced by heat in the initial stage with increasing steaming time (untreated, steamed for 30 minutes, steamed for 2 hours, steamed for 4 hours). However, after that (steamed for more than 4 hours, steamed for 8 hours), it was confirmed that the content of flavonoid glycones, which had been reduced, was increased and partially recovered as the extraction efficiency was increased due to the physicochemical change of the peels by the steaming treatment.

In the case of flavonoid aglycones, the amount of hesperidin was high in the orange peels, but the total amount of narirutin and naringin was small, and thus, only hesperetin was detected as a result of steaming. Hesperetin started to appear from 2 hours of steaming, and at 8 hours of steaming, the content thereof was increased by about 3 times or more compared to the initial stage, confirming that the flavonoid glycones were converted to low-molecular aglycones. After 8 hours of steaming, it showed a tendency to decrease again.

The components of furanocoumarins were not detected under untreated and steam-treated conditions.

TABLE 4

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 134.2 | 127.7 | 57.3 | 49.3 | 20.6 | 66.9 |
| Naringin | N.D. | N.D. | N.D. | N.D. | N.D. | N.D. |
| Hesperidin | 1629.9 | 1496.5 | 407.8 | 329.1 | 527.0 | 623.2 |
| Total | 1764.1 | 1624.2 | 465.1 | 378.4 | 547.6 | 690.1 |

TABLE 4-continued

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Naringenin | N.D. | N.D. | N.D. | N.D. | N.D. | N.D. |
| Hesperetin | N.D. | N.D. | 5.5 | 10.4 | 17.5 | 11.0 |
| Total | N.D. | N.D. | 5.5 | 10.4 | 17.5 | 11.0 |
| Bergapten | N.D. | N.D. | N.D. | N.D. | N.D. | N.D. |
| Bergamottin | N.D. | N.D. | N.D. | N.D. | N.D. | N.D. |
| Total | N.D. | N.D. | N.D. | N.D. | N.D. | N.D. |

Example 2-5. Change in Components According to Steaming Treatment Time of Bitter Orange Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of bitter orange, a citrus species (Table 5).

As a result, in the case of flavonoid glycones (narirutin, naringin), it was confirmed that the content of naringin was significantly higher compared to that of narirutin. Additionally, the two substances were decomposed and reduced by heat in the initial stage with increasing steaming time (untreated, steamed for 30 minutes, steamed for 2 hours, steamed for 4 hours). However, after that (steamed for more than 4 hours, steamed for 8 hours), it was confirmed that the content of flavonoid glycones, which had been reduced, was increased and partially recovered as the extraction efficiency was increased due to the physicochemical change of the peels by the steaming treatment. After 8 hours of steaming, naringin showed a tendency to decrease again, and narirutin was not detected.

In the case of flavonoid aglycones, they started to appear from 2 hours of steaming, and at 8 hours of steaming, the content thereof was increased by about 4 times or more compared to the initial stage, confirming that the flavonoid glycones were converted to low-molecular aglycones. After 8 hours of steaming, it showed a tendency to decrease again.

In the case of furanocoumarin (bergapten), from 2 hours of steaming, the content thereof was reduced to less than half compared to the initial amount, confirming that harmful substances were reduced according to the steaming treatment. At 8 hours of steaming, it was confirmed that the content of bergapten was partially recovered, but after 8 hours of steaming, it showed a tendency to decrease again, confirming that it had a similar pattern to the change in the flavonoid glycones.

TABLE 5

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 6.4 | 6.0 | 1.4 | 0.9 | 1.4 | N.D. |
| Naringin | 1975.0 | 1853.2 | 625.1 | 518.0 | 936.7 | 561.8 |
| Hesperidin | N.D. | N.D. | N.D. | N.D. | N.D. | N.D. |
| Total | 1981.4 | 1859.2 | 626.5 | 518.9 | 938.1 | 561.8 |
| Naringenin | N.D. | N.D. | 9.6 | 14.5 | 40.8 | 18.9 |
| Hesperetin | N.D. | N.D. | 9.7 | 14.8 | 41.0 | 21.1 |
| Total | N.D. | N.D. | 19.3 | 29.3 | 81.8 | 40.0 |
| Bergapten | 6.4 | 5.9 | 2.1 | 1.6 | 2.3 | 1.6 |
| Bergamottin | N.D. | N.D. | N.D. | N.D. | N.D. | N.D. |
| Total | 6.4 | 5.9 | 2.1 | 1.6 | 2.3 | 1.6 |

Example 2-6. Change in Components According to Steaming Treatment Time of Grapefruit Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of grapefruit, a citrus species (Table 6).

As a result, in the case of flavonoid glycones, narirutin and naringin were detected, while hesperidin was not detected. Additionally, narirutin and naringin were decomposed and reduced by heat in the initial stage with increasing steaming time (untreated, steamed for 30 minutes, steamed for 2 hours). However, after that (steamed for more than 2 hours), it was confirmed that the content of flavonoid glycones, which had been reduced, was increased and partially recovered as the extraction efficiency was increased due to the physicochemical change of the peels by the steaming treatment. After 4 hours of steaming, it showed a tendency to decrease again.

In the case of flavonoid aglycones, since hesperidin was not detected, hesperetin was also not detected, and only naringenin was detected. Naringenin started to appear from 2 hours of steaming, and at 8 hours of steaming, the content thereof was increased by about 2.5 times or more compared to the initial stage, confirming that the flavonoid glycones were converted to low-molecular aglycones. After 8 hours of steaming, it showed a tendency to decrease again.

In the case of furanocoumarin (bergamottin), it was detected only when not treated, steamed for 30 minutes, and steamed for 2 hours, and was not detected after 4 hours of steaming, confirming that the harmful substances were reduced according to the steaming treatment.

TABLE 6

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 282.7 | 269.5 | 211.4 | 237.5 | 203.4 | 152.3 |
| Naringin | 3131.4 | 2767.1 | 2443.8 | 2822.8 | 2679.9 | 2164.8 |
| Hesperidin | N.D. | N.D. | N.D. | N.D. | N.D. | N.D. |
| Total | 3414.1 | 3036.6 | 2655.2 | 3060.3 | 2883.3 | 2317.1 |
| Naringenin | N.D. | N.D. | 27.7 | 51.7 | 72.6 | 51.3 |
| Hesperetin | N.D. | N.D. | N.D. | N.D. | N.D. | N.D. |
| Total | N.D. | N.D. | 27.7 | 51.7 | 72.6 | 51.3 |
| Bergapten | N.D. | N.D. | N.D. | N.D. | N.D. | N.D. |
| Bergamottin | 2.5 | 2.1 | 0.8 | N.D. | N.D. | N.D. |
| Total | 2.5 | 2.1 | 0.8 | N.D. | N.D. | N.D. |

Example 2-7. Change in Components According to Steaming Treatment Time of Lemon Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of lemon, a citrus species (Table 7).

As a result, in the case of flavonoid glycones, it was confirmed that the content of hesperidin was significantly higher compared to that of narirutin and naringin. Additionally, the flavonoid glycones were decomposed and reduced by heat in the initial stage with increasing steaming time (untreated, steamed for 30 minutes, steamed for 2 hours, steamed for 4 hours). However, after that (steamed for more than 4 hours, steamed for 8 hours), it was confirmed that the content of flavonoid glycones, which had been reduced, was increased and partially recovered as the extraction efficiency was increased due to the physicochemical change of the peels by the steaming treatment. After 8 hours of steaming, naringin showed a tendency to decrease again, and narirutin was not detected.

In the case of flavonoid aglycones, since the content of narirutin and naringin in the Lime peel was significantly lower compared to that of hesperidin, only hesperetin was detected as a result of steaming. Hesperetin started to appear from 2 hours of steaming, and at 8 hours of steaming, the content thereof was increased by about 6.5 times or more compared to the initial stage, confirming that the flavonoid glycones were converted to low-molecular aglycones. After 8 hours of steaming, it showed a tendency to decrease again.

In the case of furanocoumarin, it was detected only when not treated and steamed for 30 minutes, and was not detected after 2 hours of steaming, confirming that the harmful substances were reduced according to the steaming treatment.

TABLE 7

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 18.5 | 15.2 | 4.9 | 6.0 | 7.8 | 6.5 |
| Naringin | 13.4 | 12.9 | 4.1 | 6.3 | 5.5 | 2.8 |
| Hesperidin | 640.0 | 580.8 | 178.8 | 201.1 | 263.9 | 243.7 |
| Total | 671.9 | 608.9 | 187.8 | 213.4 | 277.2 | 253.0 |
| Naringenin | N.D. | N.D. | N.D. | N.D. | N.D. | N.D. |
| Hesperetin | N.D. | N.D. | 1.9 | 6.3 | 12.7 | 6.9 |
| Total | N.D. | N.D. | 1.9 | 6.3 | 12.7 | 6.9 |
| Bergapten | 0.3 | 0.3 | N.D. | N.D. | N.D. | N.D. |
| Bergamottin | 1.6 | 1.4 | N.D. | N.D. | N.D. | N.D. |
| Total | 1.9 | 1.7 | N.D. | N.D. | N.D. | N.D. |

Example 2-8. Change in Components According to Steaming Treatment Time of Lime Peels The changes in the components of flavonoid glycones, flavonoid aglycones, and furanocoumarins were compared under various steaming time conditions (untreated, steamed for 30 minutes, steamed for 2 hours, steamed for 4 hours, steamed for 8 hours, and steamed for 12 hours) of lime, a citrus species (Table 8).

As a result, in the case of flavonoid glycones, they were decomposed and reduced by heat in the initial stage with increasing steaming time (untreated, steamed for 30 minutes, steamed for 2 hours). However, after that (steamed for more than 2 hours), it was confirmed that the content of flavonoid glycones, which had been reduced, was increased and partially recovered as the extraction efficiency was increased due to the physicochemical change of the peels by the steaming treatment.

In the case of flavonoid aglycones, they started to appear from 2 hours of steaming, and at 8 hours of steaming, the content thereof was increased by about 2.2 to 3.5 times or more compared to the initial stage, confirming that the flavonoid glycones were converted to low-molecular aglycones. After 8 hours of steaming, it showed a tendency to decrease again.

In the case of furanocoumarin, the content of bergapten was significantly reduced from 2 hours of steaming, but was partially recovered due to the increase in the extraction efficiency after 4 hours of steaming. Additionally, the content of bergamottin was also significantly reduced to less than half within 2 hours of steaming, and bergamottin was not detected after 4 hours of steaming unlike bergapten, confirming that the harmful substances were reduced according to the steaming treatment.

TABLE 8

| Contents (mg/100 g) | Untreated | Steamed for 30 minutes | Steamed for 2 hours | Steamed for 4 hours | Steamed for 8 hours | Steamed for 12 hours |
|---|---|---|---|---|---|---|
| Narirutin | 55.9 | 51.5 | 26.7 | 31.1 | 30.2 | 37.2 |
| Naringin | 3.6 | 4.0 | 6.7 | 15.5 | 26.1 | 21.7 |
| Hesperidin | 486.2 | 440.6 | 216.6 | 229.3 | 283.1 | 403.6 |
| Total | 545.7 | 496.1 | 250.0 | 275.9 | 339.4 | 462.5 |
| Naringenin | N.D. | N.D. | 1.4 | 3.3 | 4.9 | 3.2 |
| Hesperetin | N.D. | N.D. | 7.0 | 20.6 | 37.8 | 25.8 |
| Total | N.D. | N.D. | 8.4 | 23.9 | 42.7 | 29.0 |
| Bergapten | 19.6 | 18.4 | 12.9 | 17.2 | 18.2 | 15.3 |
| Bergamottin | 8.1 | 7.7 | 1.6 | N.D. | N.D. | N.D. |
| Total | 27.7 | 26.1 | 14.5 | 17.2 | 18.2 | 15.3 |

In Examples 2-2 to 2-8, the contents of flavonoid glycones and flavonoid aglycones were changed according to the steaming treatment time. In particular, the content of flavonoid glycones decreased and flavonoid aglycones increased, until 8 hours of steaming treatment, confirming that the flavonoid glycones were converted to low-molecular aglycones. In addition, in the case of furanocoumarin, a harmful substance, it was confirmed that the content thereof decreased when steamed for 2 hours or more.

Example 2-9. Changes in Properties and Components According to Heat Treatment Conditions In order to confirm whether the changes in the components shown in Examples 2-2 to 2-8 are characteristics that appear only during steaming (105-130° C.) under specific conditions of the present invention, the changes in properties and components were compared during roasting at high temperatures or steaming at low temperatures of 100° C. or less.

Typically, the components of hesperidin and hesperetin were compared (mg contained in 100 g of satsuma mandarin) under various heat treatment conditions (untreated, roasted at 120° C. for 8 hours, roasted at 200° C. for 5 minutes, steamed at 80° C. for 48 hours, steamed at 100° C. for 24 hours, and steamed at 120° C. for 8 hours) of satsuma mandarin, a citrus species, and the changes in appearance were confirmed (average value, n=3, Table 9).

TABLE 9

| Content (mg/100 g) | Untreated | Roasted at 120° C. for 8 hours | Roasted at 200° C. for 5 minutes | Steamed at 80° C. for 48 hours | Steamed at 100° C. for 24 hours | Steamed at 120° C. for 8 hours |
|---|---|---|---|---|---|---|
| Hesperidin | 2149.6 | 2625.1 | 2237.3 | 566.9 | 873.8 | 1092.2 |
| Hesperetin | N.D. | 4.5 | N.D. | 1.2 | 1.9 | 28.5 |
| Color | Orange | Dark brown | Black | Dark brown | Dark brown - Black | Dark brown - Black |
| Odor | Unique odor | Combination of unique odor and nutty flavor | Burning odor | Combination of unique odor and odor of steaming | Odor of steaming | Odor of steaming |

As shown in Table 9, when roasting was performed at 120 t for 8 hours instead of steaming, it was confirmed that the amount of hesperidin converted to hesperetin was not significant. When roasted for 5 minutes at a higher temperature of 200° C., there was no significant change in the components, and it was confirmed that hesperidin could not be converted to hesperetin because the outer surface of the raw material was easily burned. That is, it was confirmed that the steaming process plays an important role in changing the contents of hesperidin and hesperetin.

Meanwhile, when steamed at 80° C. for 48 hours and at 100° C. for 24 hours, hesperidin, a flavonoid glycone, was greatly reduced as compared when steamed for 8 hours at 120° C., and the amount of hesperetin, a flavonoid aglycone, was also significantly reduced. Based on the results, it can be implied that since the pressure was not high during steaming at 100° C. or lower in an airtight container, not only hesperidin was not converted to hesperetin, but also, the flavonoid glycones were not converted to low-molecular aglycones even when steamed for a longer period of time at low temperatures and thus subjected to more heat treatment. Additionally, it was confirmed that the aglycones were significantly generated only when steamed at a high temperature of 105° C. to 130° C. in an airtight container.

Example 3. Antioxidant Effect According to Change in Phenolic Compound Content and Free Radical Scavenging According to Steaming Treatment

Example 3-1. Change in Phenolic Compound Content According to Steaming Treatment Time Conditions of Citrus Peels The evaluation of total phenolic contents (TPC) was conducted using the Folin-Ciocalteu colorimetric method under various steaming time conditions (untreated, steamed for 30 minutes, steamed for 2 hours, steamed for 4 hours, steamed for 8 hours, and steamed for 12 hours).

Specifically, the reaction was initiated by mixing 2 mL of distilled water, 250 μL of citrus peel extract, and 250 μL of Folin-Ciocalteu's phenol reagent (2 N), and after 5 minutes, 500 μL of 7.5% sodium carbonate solution was added thereto, and a blue discoloration was observed. After reacting for 90 minutes, the absorbance was measured at 760 nm.

The absorbance was evaluated at concentrations of 25, 50, 100, 200, 400, and 800 ppm of gallic acid to prepare a calibration curve in the same manner. The total phenolic contents calculated by substituting the absorbance of the extract for the calibration curve were expressed as mg gallic acid equivalents/g of dried peel (average value, n=3).

The total phenolic contents of satsuma mandarin, yuzu, orange, grapefruit, and lime were compared (Table 10).

TABLE 10

| TPC (mg gallic acid equivalents/g) | Untreated | Steamed for 30 minutes | Steamed for 2 hours | Steamed for 4 hours | Steamed for 8 hours | Steamed for 12 hours |
|---|---|---|---|---|---|---|
| Satsuma mandarin | 23.9 | 23.7 | 23.6 | 21.8 | 31.8 | 15.8 |
| Yuzu | 15.8 | 16.2 | 17.4 | 20.3 | 25.4 | 28.2 |
| Orange | 19.3 | 18.8 | 10.1 | 11.7 | 20.2 | 22.4 |
| Grapefruit | 17.7 | 15.9 | 11.0 | 15.5 | 22.0 | 19.1 |
| Lime | 10.0 | 9.3 | 4.9 | 9.0 | 18.0 | 24.0 |

As shown in Table 10, for the phenolic acid present in the citrus peel extracts and the flavonoid glycones, which are the main ingredient, as phenolic compounds, and the changes in the total phenolic contents showed a similar tendency to the changes in the flavonoid glycones. That is, it decreased at the beginning of steaming, and after that, the reduced amount partially recovered.

Unlike the flavonoid glycones, the TPC was mostly increased at 8 hours of steaming compared to the initial stage, thereby confirming that the steaming process increased the total phenolic contents.

Hereinafter, it was attempted to confirm whether the increase in the total phenolic contents of the citrus peel extracts contributed to the increase in antioxidant effect.

Example 3-2. Antioxidant Effect According to Free Radical Scavenging

In order to confirm the antioxidant effect of citrus peel extracts, the extracts were untreated, steamed for 30 minutes or steamed for 8 hours, and thereafter, the free radical scavenging ability was measured by the 1,1-diphenyl-2-picrylhydrazyl (DPPH) assay. As a relatively stable free radical, DPPH, which exhibits the maximum absorption at 517 nm when present in a radical state and loses its absorption ability when the radical is scavenged, was dissolved in methanol at a concentration of 0.12 mM and used. As a positive control, Trolox, a water-soluble analog of vitamin E, was used.

100 μL of Trolox solutions (0.0125, 0.025, 0.05, 0.1, 0.2, 0.4, 0.8 mg/mL) for each concentration was seeded into a 24-well plate, and DPPH solution was added at 1,900 μL. The plate was left for 1 hours by blocking light at room temperature, and the absorbance was measured at 517 nm using an ELISA reader to prepare calibration curves according to the concentration using the absorbance values at 7 concentrations. Similarly, 100 μL of the citrus peel extract and 1,900 μL of DPPH solution were reacted. By substituting the absorbance of the extract for the calibration curve, the degree of antioxidant effect of 1 g of the citrus peel was expressed as Trolox μmol equivalents/g. The experiment was performed three times and the average value was calculated.

TABLE 11

| Antioxidant Efficacy (μmol Trolox equivalents/g) | Untreated | Steamed for 30 minutes | Steamed for 8 hours |
|---|---|---|---|
| Satsuma mandarin | 10.8 | 11.0 | 18.6 |
| Yuzu | 11.1 | 11.9 | 21.3 |
| Orange | 7.0 | 6.5 | 16.3 |
| Bitter orange | 10.5 | 8.6 | 10.6 |
| Grapefruit | 4.9 | 4.4 | 15.1 |
| Lemon | 5.0 | 4.1 | 11.4 |
| Lime | 3.7 | 3.5 | 14.1 |

As a result, it was confirmed that the antioxidant efficacy greatly increased when steamed for 8 hours in all citrus species. In particular, the orange, grapefruit, lemon, and lime had low antioxidant efficacy when untreated and steamed for 30 minutes, but when steamed for 8 hours, the efficacy increased by about 2 to 4 times or more, confirming that the antioxidant effect was excellent.

Example 4. Anti-Inflammatory Effect by Inhibition of NO Production

Example 4-1. Anti-Inflammatory Effect by Inhibition of NO Production

In order to confirm the anti-inflammatory effect of the citrus peel extracts, NO production inhibition rate was measured after the extracts were untreated, steamed for 30 minutes, or steamed for 8 hours. In order to culture Raw264.7 cells, a mixture of DMEM (Dulbecco's Modified Eagle's Medium) and FBS (Fetal Bovine Serum) was used as a basic medium, and the Raw264.7 cells were seeded into a 24-well plate at a concentration of 1 to $2\times10^5$ cells/mL and cultured for 24 hours. The medium was removed and the cells were starved in serum-free medium for 12 hours, and thereafter, the DMSO lysate of each extract was treated so that the concentration was 200 ppm, and after 30 minutes, lipopolysaccharide was added at a concentration of 500 ng/ml and cultured for 18 hours. L-NMMA, a positive control, was treated at 20 ppm. After completion of the culture, the supernatant was taken and transferred to a 96-well plate, reacted at room temperature by adding the GRIESS reagent, and the absorbance at 540 nm was measured using an ELISA reader. The amount of NO inhibited compared to the control group was calculated as NO production inhibition rate (%), and the average value was calculated after the experiment was performed three times.

TABLE 12

| NO Production Inhibition Rate (%) | Untreated | Steamed for 30 minutes | Steamed for 8 hours |
|---|---|---|---|
| L-NMMA (Positive control) | | 55.1% | |
| Satsuma mandarin | 12.2% | 13.1% | 18.2% |
| Yuzu | 14.9% | 15.1% | 17.5% |
| Orange | 10.3% | 10.9% | 12.4% |
| Bitter orange | 8.2% | 7.9% | 11.1% |
| Grapefruit | 6.7% | 6.3% | 8.3% |
| Lemon | 4.4% | 4.5% | 6.3% |
| Lime | −2.1% | −1.5% | 2.9% |

As a result, as shown in Table 12, when the extracts were steamed for 8 hours, it was confirmed that the anti-inflammatory effect was superior compared to when they were untreated and steamed for 30 minutes.

Example 4-2. Anti-Inflammatory Effect According to Components and Concentration of Citrus Peel In order to identify the cause of the change in anti-inflammatory efficacy among the steamed citrus peel extract components, the NO production inhibition rates of hesperidin, a flavonoid glycone, and hesperetin, a a flavonoid aglycone, were compared (Table 13)

TABLE 13

| NO Production Inhibition Rate (%) | Hesperidin | Hesperetin |
|---|---|---|
| L-NMMA (Positive control) | 51.3% | |
| 0.1 ppm | −5.5% | −3.0% |
| 1 ppm | 0.6% | 2.6% |
| 10 ppm | 1.8% | 8.1% |
| 20 ppm | 2.4% | 35.6% |

As a result, as shown in Table 13, when hesperidin and hesperetin were treated at higher concentrations, the NO production inhibition rate was further increased, and in particular, at a certain concentration or higher (20 ppm), the NO production inhibition rate of hesperetin was significantly increased. Accordingly, it was confirmed that the flavonoid aglycones generated from the steamed citrus peel extracts could be the cause of the increased anti-inflammatory efficacy.

Example 5. Collagen Synthesis-Promoting Effect

Example 5-1. Collagen Synthesis-Promoting Effect

In order to confirm the collagen synthesis promoting effect of the citrus peel extracts, the amount of additional collagen production was measured after the extracts were untreated, steamed for 30 minutes, or steamed for 8 hours. In order to culture human dermal fibroblasts, a mixture of DMEM and FBS was used as a basic medium, and the skin fibroblasts were seeded into a 48-well plate at a concentration of 2 to $5\times10^4$ cells/mL and cultured for 24 hours. The medium was removed, and the DMSO lysate of each extract was treated in serum-free medium so that the concentration was 100 ppm, and cultured for 24 hours. A positive control that promotes collagen synthesis was treated with TGF-β to a concentration of 5 ppb. The cell culture solution was taken and the synthesized collagen was measured using the Human procollagen 1α1 duoset ELISA Kit (R&D Systems) and ELISA reader. A calibration curve was prepared by measuring the isolated and purified collagen at concentrations of 0.25, 0.5, 1, 2, 4, and 8 ng/mL, and based on the results, the amount of collagen (Type I collagen) produced in the DMSO lysate of the citrus peel extracts was calculated. The amount of collagen produced compared to the control group (DMSO) was calculated as collagen production rate (%), and the average value was calculated after the experiment was performed three times (Table 14).

TABLE 14

| Additional Collagen Production Rate (%) | Untreated | Steamed for 30 minutes | Steamed for 8 hours |
|---|---|---|---|
| TGF-β (Positive control) | | 25.2% | |
| Satsuma mandarin | 19.5% | 18.7% | 27.9% |
| Yuzu | 13.7% | 14.2% | 18.1% |
| Orange | 5.1% | 5.0% | 6.6% |
| Bitter orange | 12.8% | 13.6% | 17.4% |
| Grapefruit | 7.3% | 6.5% | 9.3% |
| Lemon | −1.0% | −1.5% | 2.6% |
| Lime | 0.5% | 2.1% | 5.2% |

As a result, as shown in Table 14, it was confirmed that the amount of collagen produced when steamed for 8 hours was superior compared to when untreated and steamed for 30 minutes.

Example 5-2. Collagen Synthesis-Promoting Effect According to Components and Concentration of Citrus Peel In order to identify the cause of the change in collagen synthesis promoting efficacy among the steamed citrus peel extract components, the amount of additional collagen production of hesperidin, a flavonoid glycone, and hesperetin, a flavonoid aglycone, was compared (Table 15).

TABLE 15

| Additional Collagen Production Rate (%) | Hesperidin | Hesperetin |
|---|---|---|
| TGF-β (Positive control) | 23.7% | |
| 0.1 ppm | −0.2% | 17.0% |
| 1 ppm | 0.2% | 16.8% |

As a result, as shown in Table 15, unlike hesperidin, the collage production was significantly increased in hesperetin at lower concentrations (0.1 ppm, 1 ppm). Accordingly, it was confirmed that the flavonoid aglycones produced in the steamed citrus peel extracts may be the cause of the increase in collagen synthesis promoting efficacy.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for preparing a citrus peel extract, comprising:

removing a citrus peel from a citrus fruit and drying the removed citrus peel;

steaming the dried citrus peel; and extracting a citrus peel extract from the steamed citrus peel, wherein the steaming is performed in an airtight container at 103° C. to 150° C. for 2 hours to 8 hours.

2. The method of claim 1, wherein the peel is the peel of satsuma mandarin (*Citrus unshiu*), yuzu (*Citrus junos*), orange (*Citrus sinensis*), bitter orange (*Citrus aurantium*), grapefruit (*Citrus paradisi*), lemon (*Citrus limonum*) or lime (*Citrus aurantifolia*).

3. The method of claim 1, wherein the steaming is characterized by converting flavonoid glycones to flavonoid aglycones or reducing the generation of furanocoumarin.

4. The method of claim 1, wherein the steamed citrus peel has a higher content of flavonoid aglycones as compared to when it is not steamed.

5. The method of claim 3, wherein the flavonoid glycones are narirutin, naringin, or hesperidin, and the flavonoid aglycones are naringenin or hesperetin.

6. The method of claim 3, wherein the furanocoumarin is bergapten or bergamottin.

7. The method of claim 1, wherein the steamed citrus peel has a higher total phenolic content as compared to when it is not steamed.

8. The method of claim 1, wherein the citrus peel extract has an antioxidant use.

9. The method of claim 1, wherein the citrus peel extract has an anti-inflammatory use.

10. A method for improving elasticity or wrinkles, the method comprising applying the citrus peel extract prepared by the method of claim 1 as an active ingredient to improve elasticity or wrinkles of a subject, wherein the citrus peel extract has a higher content of flavonoid aglycones and a higher total phenolic content as compared to the dried citrus peel.

11. A method for improving antioxidant activity, comprising applying the citrus peel extract prepared by the method of claim 1 or a composition comprising the citrus peel extract prepared by the method of claim 1 as an active ingredient to a subject.

12. A method for preventing or improving inflammation, comprising applying the citrus peel extract prepared by the method of claim 1 or a composition comprising the citrus peel extract prepared by the method of claim 1 as an active ingredient to a subject.

13. The method of claim 1, wherein the steaming converts flavonoid glycones to flavonoid aglycones at a conversion rate that is higher than a conversion rate of a reference steaming process performed for less than 2 hours or more than 8 hours under the same conditions.

14. A method for preparing a citrus peel extract, comprising:

removing a citrus peel from a citrus fruit and drying the removed citrus peel;

steaming the dried citrus peel in an airtight container at 103° C. to 150° C. for 2 hours to 8 hours and drying the steamed citrus peel;

powdering the dried steamed citrus peel; and mixing the powdered citrus peel with a solvent to form a citrus peel extract.

15. The method of claim 1, wherein the peel is a peel of yuzu (*Citrus junos*), orange (*Citrus sinensis*), bitter orange (*Citrus aurantium*), grapefruit (*Citrus paradisi*), lemon (*Citrus limonum*) or lime (*Citrus aurantifolia*).

16. The method of claim 14, wherein the steaming converts flavonoid glycones to low-molecular flavonoid aglycones at a conversion rate that is higher than a conversion rate of a reference steaming process performed for less than 2 hours or more than 8 hours under the same conditions, and the peel is a peel of yuzu (*Citrus junos*), orange (*Citrus sinensis*), bitter orange (*Citrus aurantium*), grapefruit (*Citrus paradisi*), lemon (*Citrus limonum*) or lime (*Citrus aurantifolia*).

17. The method of claim 1, wherein the citrus peel extract has a higher content of flavonoid aglycones and a higher total phenolic content as compared to the dried citrus peel.

18. The method of claim 1, wherein the steaming is characterized by converting flavonoid glycones to flavonoid aglycones and reducing the generation of furanocoumarin.

* * * * *